United States Patent
Wilcox et al.

(10) Patent No.: US 9,247,967 B2
(45) Date of Patent: Feb. 2, 2016

(54) ROD AND ANCHOR SYSTEM AND METHOD FOR USING

(75) Inventors: Bryan S. Wilcox, Collierville, TN (US); Christopher M. Patterson, Olive Branch, MS (US); Rodney R. Ballard, Lakeland, TN (US); Lawrence G. Lenke, St. Louis, MO (US); Timothy R. Kuklo, Rockville, MD (US); Stephen Ondra, Wilmette, IL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1187 days.

(21) Appl. No.: 12/326,927

(22) Filed: Dec. 3, 2008

(65) Prior Publication Data

US 2010/0137918 A1    Jun. 3, 2010

(51) Int. Cl.
*A61B 17/70* (2006.01)
*A61F 2/44* (2006.01)
*A61F 2/28* (2006.01)
*A61F 2/30* (2006.01)
*A61B 17/86* (2006.01)

(52) U.S. Cl.
CPC ........... *A61B 17/7037* (2013.01); *A61B 17/863* (2013.01); *A61B 17/704* (2013.01); *A61B 17/7032* (2013.01); *A61B 17/7034* (2013.01); *A61B 17/7035* (2013.01); *A61B 17/7038* (2013.01)

(58) Field of Classification Search
CPC ........... A61B 17/7032; A61B 17/7035; A61B 17/7037; A61B 17/7034; A61B 17/7038; A61B 17/704

USPC ......... 623/16.11, 17.11, 18.11; 606/250–279, 606/300–331, 907, 914, 916, 99, 103–104, 606/281, 900–901

See application file for complete search history.

(56) References Cited

U.S. PATENT DOCUMENTS

| | | | | |
|---|---|---|---|---|
| 597,000 | A | * | 1/1898 | Higbee .......................... 285/333 |
| 5,346,492 | A | * | 9/1994 | Morgan .......................... 606/60 |
| 5,782,833 | A | * | 7/1998 | Haider ........................... 606/266 |
| 5,885,286 | A | * | 3/1999 | Sherman et al. .............. 606/270 |
| 6,004,323 | A | | 12/1999 | Park et al. |

(Continued)

FOREIGN PATENT DOCUMENTS

EP    1923151 A1    7/2007

OTHER PUBLICATIONS

Corrosion of Orthopaedic Implants, Screws, Plates and Femoral Nail-plates, John T. Scales, G.D. Winter, London, England, Department of Biomechanics and Surgical Materials, Institute of Orthopaedics (University of London), Royal National Orthopaedic Hospital, London and Stanmore and H.T. Shirley, Sheffield, England, The Brown-Firth Research Laboratories, Sheffield, The Journal of Bone and Joint Surgery, pp. 810-820, vol. 41 B, No. 4, Nov. 1959.

*Primary Examiner* — Jacqueline Woznicki

(57) ABSTRACT

A method of conducting a surgical procedure including implanting an anchor into a bone, wherein the anchor comprises a receiving portion and a screw, the screw including a screw head contained within the receiving portion and pivotally engageable with a surface of the receiving portion, and wherein the receiving portion and the screw comprising a different material. The method further includes selecting a rod from a group of rod types and coupling the rod with the receiving portion to stabilize a position of a portion of the spine.

20 Claims, 8 Drawing Sheets

(56) References Cited

U.S. PATENT DOCUMENTS

| | | | |
|---|---|---|---|
| 6,129,730 A * | 10/2000 | Bono et al. | 606/291 |
| 6,162,225 A | 12/2000 | Gertzman et al. | |
| 6,270,529 B1 * | 8/2001 | Terrill-Grisoni et al. | 623/20.11 |
| 6,783,527 B2 * | 8/2004 | Drewry et al. | 606/254 |
| 7,261,714 B2 | 8/2007 | Richelsoph | |
| 7,404,818 B2 * | 7/2008 | Miller et al. | 606/301 |
| 2003/0093078 A1 * | 5/2003 | Ritland | 606/73 |
| 2005/0059972 A1 * | 3/2005 | Biscup | 606/73 |
| 2005/0085814 A1 | 4/2005 | Sherman et al. | |
| 2005/0234451 A1 * | 10/2005 | Markworth | 606/61 |
| 2006/0116677 A1 * | 6/2006 | Burd et al. | 606/61 |
| 2006/0200131 A1 * | 9/2006 | Chao et al. | 606/61 |
| 2006/0229607 A1 * | 10/2006 | Brumfield | 606/61 |
| 2007/0016200 A1 | 1/2007 | Jackson | |
| 2007/0073291 A1 * | 3/2007 | Cordaro et al. | 606/61 |
| 2007/0225707 A1 * | 9/2007 | Wisnewski et al. | 606/61 |
| 2007/0233071 A1 * | 10/2007 | Dewey et al. | 606/61 |
| 2007/0233086 A1 * | 10/2007 | Harms et al. | 606/61 |
| 2007/0270819 A1 | 11/2007 | Justis et al. | |
| 2007/0270831 A1 * | 11/2007 | Dewey et al. | 606/61 |
| 2008/0027444 A1 | 1/2008 | Malek | |
| 2008/0086129 A1 | 4/2008 | Lindemann et al. | |
| 2008/0161863 A1 * | 7/2008 | Arnold et al. | 606/319 |
| 2009/0182384 A1 * | 7/2009 | Wilcox et al. | 606/305 |
| 2009/0287251 A1 * | 11/2009 | Bae et al. | 606/254 |
| 2010/0004685 A1 * | 1/2010 | Justis et al. | 606/246 |
| 2010/0160978 A1 * | 6/2010 | Carbone | 606/305 |

\* cited by examiner

ROD AND ANCHOR SYSTEM AND METHOD FOR USING

BACKGROUND

1. Field of the Disclosure

The following is directed to a method of using a rod and anchor system, and more particularly directed to a method of using rod and anchor system utilizing anchors capable of use with a variety of rod type for correction of spinal abnormalities.

2. Description of the Related Art

In human anatomy, the spine is a generally flexible column that can take tensile and compressive loads. The spine also allows bending motion and provides a place of attachment for tendons, muscles and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Also, the vertebrae are separated by intervertebral discs, which are situated between adjacent vertebrae.

There are a variety of different spinal abnormalities, including for example, improper curvatures, deformed vertebrae, misaligned vertebrae, which may be cured or mitigated by implantation of certain devices. Such devices can include articles and mechanisms useful for repairing damaged portions of the spine, stabilizing portions of the spine, or even changing the position of the spine to a more natural state. In certain instances, rod and anchor systems are commonly employed when portions of the spine need to be realigned, such as in patients with abnormal curvatures. These systems typically include anchors that can be implanted within the bone of the spine and attached to a rod extending along the abnormal portion of the spine, such that the rod provides rigid support for urging the spine to a more healthy position.

Implantation of a rod and anchor system typically involves the fixation of a plurality of screws that are precisely placed within the patient's spine. Current rod and anchor systems offer treatment options by providing a selection of rods and anchors in different sizes. Generally, in a pre-operative diagnosis, the surgeon estimates the best combination of rods and anchors based upon certain criteria, such as the size, age, and general health of the patient, and the severity of the abnormality. However, unexpected conditions associated with the health of the spine, severity of the condition, and other factors may lead to a change in the rod and anchor architecture during the surgical procedure. Such changes are fraught with potential problems including, a longer surgical procedure exposing the patient to a greater risk of infection and additional trauma, tiring of the surgeon and staff, trial and error design changes, and ultimately a potential for implantation of a rod and anchor system not properly suited for the intended task.

Because of the nature of treating spinal deformities or degenerative conditions, and the critical function of the spine, implants and methods of treating deformities must be suitably developed to ensure patient recovery and proper implant performance. Accordingly, the industry continues to demand improvements in such implants.

SUMMARY

According to a first aspect, a method is disclosed for conducting a surgery that includes implanting an anchor into a bone, wherein the anchor comprises a receiving portion and a screw, the screw including a screw head contained within the receiving portion and pivotally engageable with a surface of the receiving portion. The receiving portion includes a material having a greater yield strength than a material of the screw. The method further includes selecting a rod from a group of rod types and coupling the rod with the receiving portion.

According to a second aspect, a method is disclosed for conducting a surgery that includes implanting an anchor into a bone, wherein the anchor comprises a receiving portion and a screw, the screw includes a screw head contained within the receiving portion and pivotally engageable with a surface of the receiving portion. The receiving portion and the screw include a different material. The method further includes selecting a rod from a group of rod types, and coupling the rod with the receiving portion.

According to another aspect, a method of conducting a surgery includes implanting an anchor into a bone, wherein the anchor comprises a screw coupled to a receiving portion that is configured to engage a rod and couple the screw and rod together. The method further includes selecting a rod from a group of rod types, where the rod types may be selected based upon diameter of the rod, material of the rod, or a combination thereof. Further steps in the method include coupling the rod within the receiving portion and selecting a set screw from a group of set screw types based on a material of the rod, wherein each set screw type can be made of a different material. The method can further include fastening the set screw within the receiving portion to secure the rod and receiving portion to each other.

In another aspect, another method of conducting a surgery includes implanting an anchor into a bone, wherein the anchor comprises a receiving portion and a screw and the receiving portion and the screw comprise a different material. The method further includes selecting a rod from a group of rod types, coupling the rod within the receiving portion, and setting a torque limit on a tool for engaging a set screw based upon a material of the rod. After setting the torque limit, the method can include fastening a set screw within the receiving portion to engage the rod at the set torque limit of the tool to secure the rod and the receiving portion to each other. As such, in these embodiments, all rods can use a single type of set screw, placed within the anchor at a predetermined set torque level.

BRIEF DESCRIPTION OF THE DRAWINGS

The present disclosure may be better understood, and its numerous features and advantages made apparent to those skilled in the art by referencing the accompanying drawings.

DETAILED DESCRIPTION

Description of Relevant Anatomy

Figure 1:
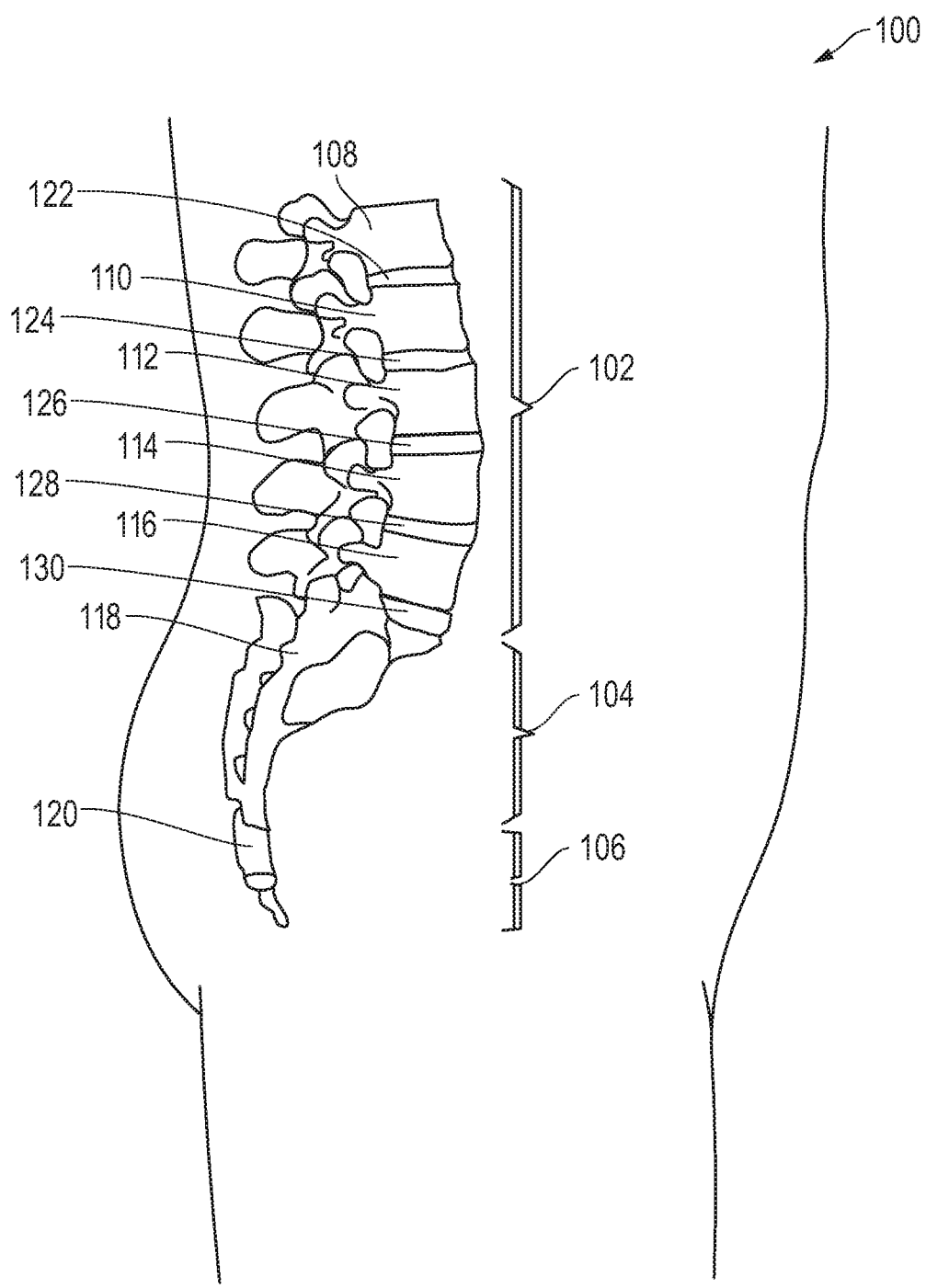
FIG. 1 includes a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

Figure 2:
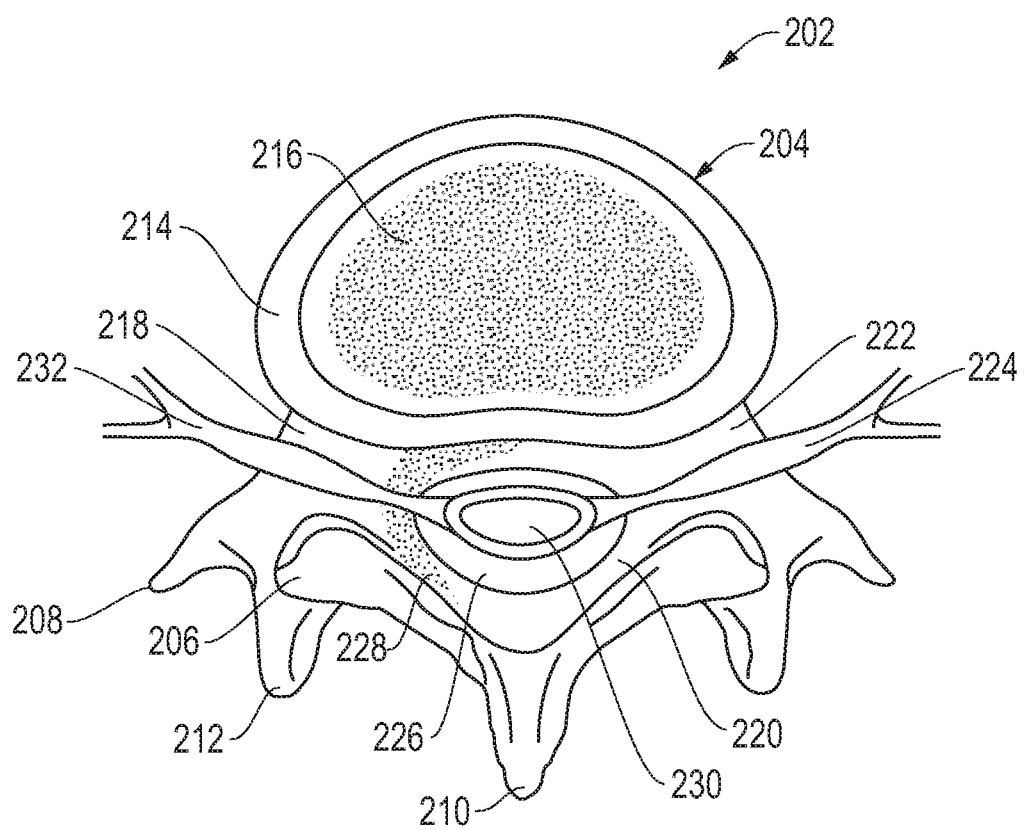
FIG. 2 includes a top plan view of a vertebrae.

Referring to FIG. 2, a vertebra 202 is illustrated. As shown, the vertebral body 204 includes a cortical rim 214 composed of cortical bone. Also, the vertebral body 204 includes cancellous bone 216 within the cortical rim 214. The cortical rim 214 is often referred to as the apophyseal rim or apophyseal ring. Further, the cancellous bone 216 is generally softer than the cortical bone of the cortical rim 214.

As illustrated in FIG. 2, the vertebra 202 further includes a first pedicle 222, a second pedicle 218, a first lamina 220, and a second lamina 228. Further, a vertebral foramen 226 is established within the vertebra 202. A spinal cord 230 passes through the vertebral foramen 226. Moreover, a first nerve root 224 and a second nerve root 232 extend from the spinal cord 230. Notably, during implantation of anchors, such as screws within the spine, particularly anchors that will be attached to other implants, such as a rod, such screws can generally be implanted within the pedicles 218 and 222, since these portions of the spine provide suitable support and rigidity for anchors.

The vertebrae that make up the vertebral column have slightly different appearances as they range from the cervical region to the lumbar region of the vertebral column. However, all of the vertebrae, except the first and second cervical vertebrae, have the same basic structures.

Description of Embodiments

The following description is directed to a rod and anchor system designed to alleviate and correct spinal deformities such as, curvatures of the spine common with such maladies as kyphosis or scoliosis. The following description details certain features of the rods and anchors, and more particularly, a system for using such rod and anchors in which the surgeon is provided with fewer pieces, yet greater options for greater flexibility in implant design for a given patient. More features and benefits will become apparent in the following description.

Figure 3:
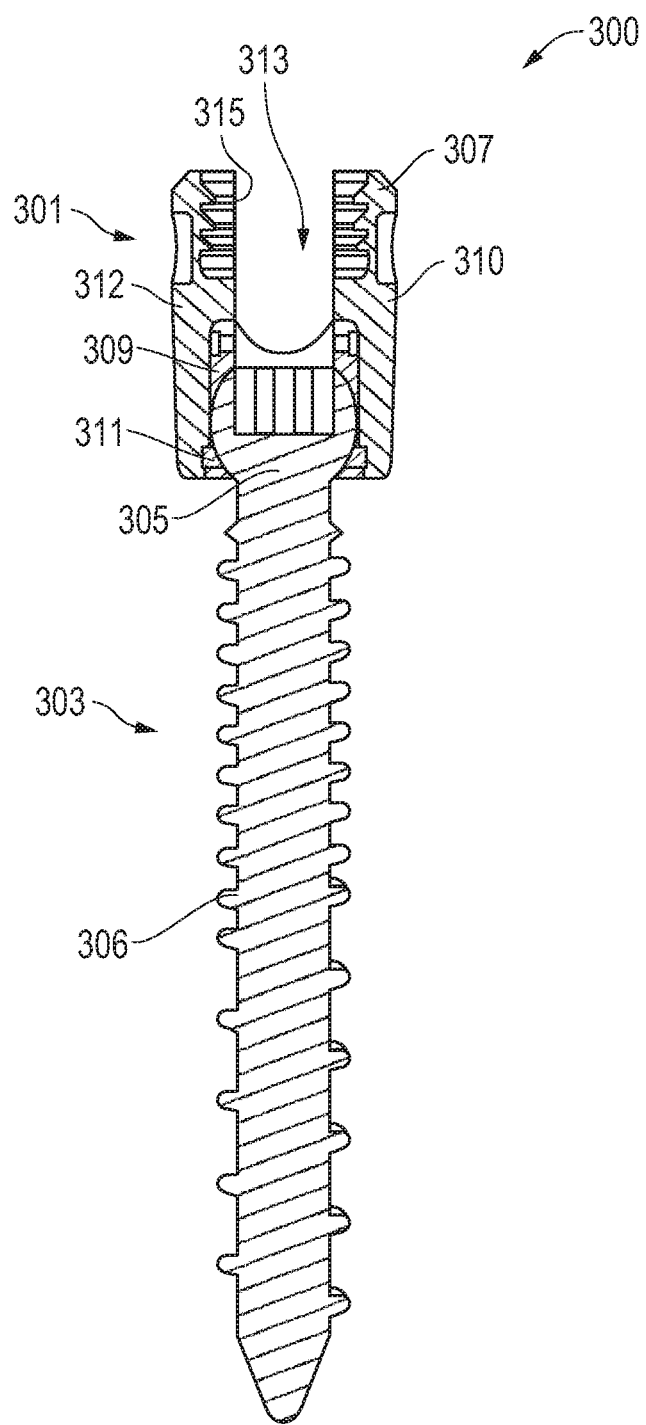
FIG. 3 includes a cross-sectional view of an anchor in accordance with an embodiment.

FIG. 3 includes a cross-sectional illustration of an anchor in accordance with an embodiment. In particular, the anchor 300 includes a receiving portion 301 connected to a screw 303. The screw 303 includes a threaded shaft 306 suitable for aiding implantation of the screw 303 within bone. Additionally, the screw 303 includes a screw head 305 at a proximal end of the screw 303 that is generally rounded and configured to be contained within a portion of the receiving portion 301. In particular, the screw head 305 is contained within a receiving portion 301 and pivotally engageable with a surface of the receiving portion 301. As such, the depicted anchor 300 is a polyaxial screw capable of angulation and pivoting with respect to the receiving portion 301 for easier placement and precise implantation into a patient.

The receiving portion 301 includes a head portion 307, a crown 309, and a ring 311. In particular, the head portion 307 is a generally u-shaped structure having arms 310 and 312 and an opening 313 extending between the arms 310 and 312 transversely to the longitudinal axis of the head portion 307 such that a rod can be engaged within the opening 313. The receiving 301 portion is configured to engage a portion of a rod and thereby connect and affix a screw 303 to the rod and thus coupling a portion of a patient's spine relative to the rod. As can be understood, such a configuration allows for maneuvering and correction of a condition of a spine to more properly align with a chosen alignment dictated by the position of the implanted rod. The receiving portion 301 as noted above further includes a crown 309 which is configured to be contained within the head portion 307 and coupled to the screw head 305. Upon coupling of the receiving portion 301 with a rod, the crown 309 is position such that it engages a portion of the rod. As such, the crown 309 provides an interface for both the screw head 305 and rod, and has contours suitable for proper placement of both the screw head 305 and the rod within the receiving portion 307.

As further illustrated in FIG. 3, the receiving portion 301 includes a ring 311 contained within an interior of the head portion 307 and configured to engage the screw head 305. Notably, the ring 311 is positioned such that it facilitates containment of the screw head 305 within the receiving portion 301 while allowing angulation and pivoting of the screw 303 relative to the head portion 307.

Figure 4:
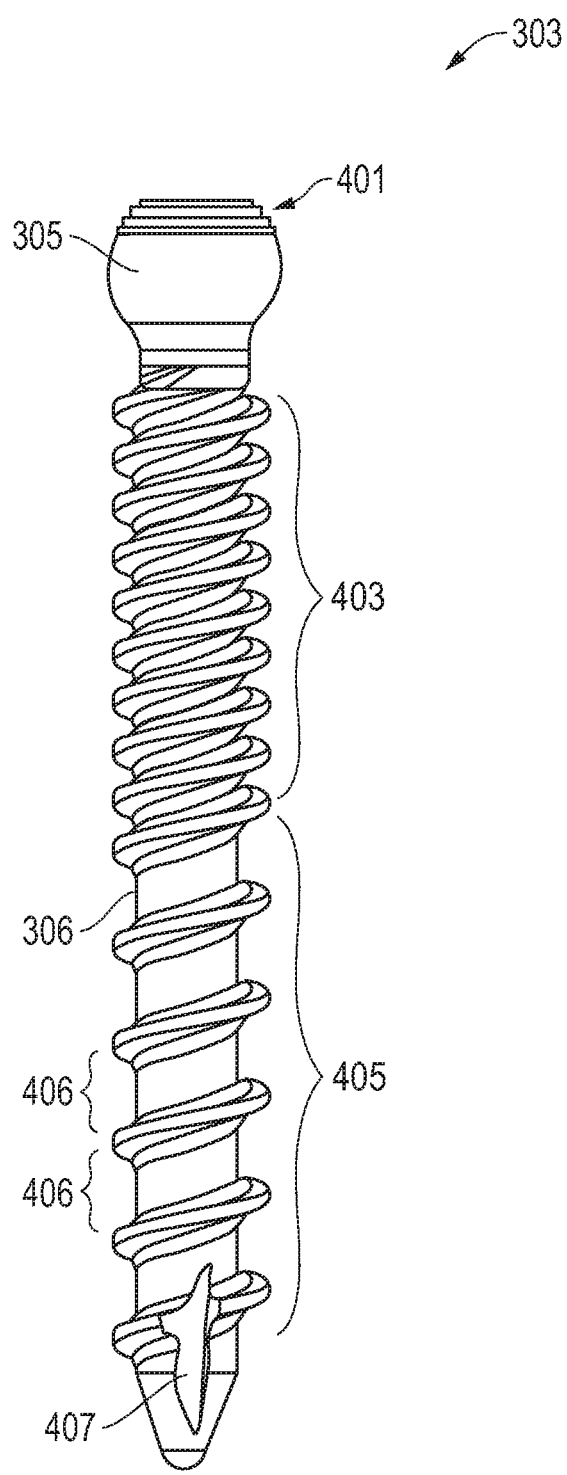
FIG. 4 includes a side-view of a screw in accordance with an embodiment.

FIG. 4 includes a side view of a screw 303 in accordance with an embodiment. Notably, the screw, as previously illustrated in FIG. 3 includes a screw head 305 at a proximal end of the screw 303 as well as a threaded shaft 306 connected to the screw head 305. As illustrated, the screw head 305 can have a generally hemispherical or semi-hemispherical shape such that it is properly configured for angulation and pivoting along a surface of the head portion 307 of the receiving portion 301. Such a configuration facilitates the polyaxial capabilities of the screw 303. Additionally, the screw head 305 includes a stepped portion 401 at the proximal end, which allows for compression of the crown 309 onto the screw head 305 and thereby locking the position of the anchor 300 relative to the spinal anatomy and the location of the rod.

As further illustrated in FIG. 4, the screw 303 includes a threaded shaft 306 having different threaded portions. In particular, the screw 303 includes a threaded portion 403 adjacent to the screw head 305 and another threaded portion 405 adjacent to the distal end of the screw 303. As illustrated, the threaded portion 403 has a thread form of tightly wound threads along the shaft of the screw 303 such that no gaps exist exposing portions of the shaft between the threads. By contrast, the threaded portion 405 has a different thread form than the thread form of portion 403. In particular, the threaded portion 405 includes gaps 406 between adjacent threads such that the underlying shaft of the screw 303 is exposed. The thread forms illustrated in threaded portions 403 and 405 facilitate increased thread purchase within bone of patients and necessitate fewer revolutions for inserting the thread shaft 306 into bone. In particular, the threaded portion 405 is suitable for screwing into softer bone while allowing faster advancement based on the spacing between threads, while the threaded portion 403 having the tighter thread form facilitates threading of the screw 303 into denser bone.

Additionally, the screw 303 includes a flute 407 adjacent to the tapered end of the screw 303. The flute 407 facilitates insertion and starting of the screw 303 for proper implantation into the bone and may also include a burr to avoid reversing and pullout of the screw 303 once implanted.

Notably, the components of the anchor herein are formed such that they can include different materials. That is, as will be appreciated with further description, components of the receiving member can include materials that are different than the materials of the screw 303 to facilitate coupling with various rod types. In accordance with an embodiment, the screw 303 can be made of a metal material, and more particularly, a metal such as titanium, including titanium alloy, for example Ti6Al4V, Ti15Mb, and the like. In still other instances, the screw 303 can include cobalt, such as cobalt chrome. In accordance with a particular embodiment, the screw 303 is made entirely of Ti6Al4V. Titanium screws are suitable due to superior imaging quality, which aids proper placement of the screw.

In more detailed terms, reference to a different material herein is based on a difference of elemental weight percent for each element contained in the two materials being compared. In particular, different materials have a difference in elemental weight percent of at least about 5 wt % based on the absolute value of the total difference in weight content of each elements contained in the components. In other embodiments the difference of elemental weight percents between the two materials can be greater, such as at least about 10 wt %, 15 wt %, 20 wt %, or even at least about 25 wt %.

For example, the screw 303 can be made of Ti6Al4V, a material containing 6 wt % aluminum, and 4 wt % vanadium, some trace elements wherein each is present in an amount of less than 1 wt %, and the remainder (about 90 wt %) being titanium. A component of the receiving portion 301, such as the head portion 307, can be made of Ti15Mb, a material containing 15 wt % molybdenum, some trace materials, wherein each trace material is present in an amount less than 1 wt % and the remainder (about 85 wt %) being titanium. The elemental weight percent difference of the screw material relative to the head portion material is 15 wt %, based on the absolute difference in the um of elemental weight percents of each of the elemental components. In more detail, the difference in the titanium content from the screws to the receiving portion is 5 wt %. The difference in the elemental weight percent of the aluminum is 6 wt %, since there is essentially no aluminum in the material of the head portion 307, excluding impurity contents which are typically fractions of a percent. And, the difference in the elemental weight percent of the vanadium is 4 wt %, since the material of the head portion 307 does not contain vanadium, again excluding impurity contents of the alloy material of the head portion 307.

Accordingly, different materials may contain all of the same elemental components, however, the total elemental weight percent of such components differs by at least 5 wt %, and as such the materials are considered different. As such, different materials will generally include materials that differ by at least one elemental component, even if the base material is the same, such as common in alloys.

Figure 5:
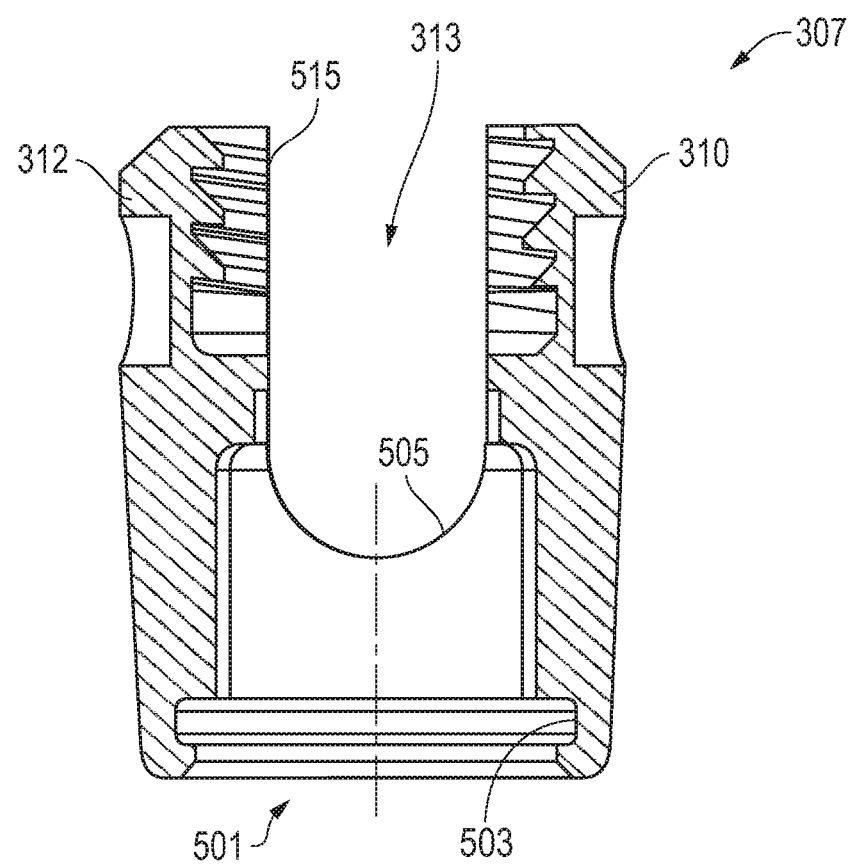
FIG. 5 includes a cross-sectional view of a receiving portion in accordance with an embodiment.

FIG. 5 includes a cross-sectional view of a head portion of the receiving portion in accordance with an embodiment. The head portion 307 has a generally u-shaped cross-sectional contour formed by its body and arms 310 and 312 generally extending parallel to the longitudinal axis of the body of the head portion 307. Additionally, the head portion 307 includes an opening 313 between the arms 310 and 312 for engagement of a rod therein. Head portion 307 includes an inner surface 315. As further illustrated in FIG. 5, the head portion 307 includes a semi-circular surface 505 for engaging a portion of a rod thereon.

The head portion 307 also includes an opening 501 extending into the interior of the head portion body along the longitudinal axis of the body defined by a surface 503. The opening 501 joins with opening 313 forming a passage extending longitudinally through the body of the head portion 307. The opening 501 facilitates the engagement of a screw head 305 therein such that the screw 303 and rod can be coupled to each other. In particular, the head portion 307 further includes a surface 503 configured to engage a ring 311 therein and affix the position of the screw head within the opening 501. The head portion 307 includes a threaded portion 515 within the arms 310 and 312 configured to engage a set screw therein and facilitate affixing a rod within the opening 313.

As described herein, components of the anchor including the components of the receiving portion 301 such as the head portion 307 can be made of certain materials for facilitating greater flexibility in the choice of rods to which the receiving member, and ultimately the anchor, are connected. This in turn facilitates greater flexibility interoperatively (i.e., during the operation) such that the surgeon can change his procedure, if necessary, without undue complications. In fact, the components of the receiving portion can be formed from materials having a tensile strength (i.e., yield strengths) and stiffness (i.e., Modulus of Elasticity) greater than the corresponding yield strength and stiffness of the material of the screw 303 making the receiving portion 301 suitable for use with a wide variety of rod materials.

In accordance with one embodiment, the head portion 307 is typically made of a metal or metal alloy. In particular, the head portion 307 is made of a different material than the material of the screw 303. Suitable metals can be those having a yield strength that is greater than the yield strength of the rod material or screw material. It will be appreciated that yield strength is the stress at which a material strain changes from elastic deformation to plastic deformation causing it to deform permanently. The formation of the head portion 307 from a material having a greater yield strength than the material of the screw and/or the rod facilitates a head portion 307 capable of holding its shape without deformation during coupling of the rod and screw members. In fact, selection of the material of the head portion 307 can make the receiving portion 301 suitable for use with a wide variety of rod materials. Certain materials suitable for use in the head portion 307 are those having a yield strength of at least about 450 MPa. In other instances, the yield strength may be greater, such as at least about 500 MPa, or even at least about 800 MPa. In accordance with a particular embodiment, the head portion 307 includes a material having a yield strength within a range between about 450 MPa and about 1400 MPa, and more particularly within a range between about 1000 MPa and about 1400 MPa.

Additionally, the head portion 307 can be made of a material having a greater stiffness than the material of the screw 303. Such mechanical characteristics avoid deformation of the head portion 307 in the presence of excessive loading on the anchor 300. In one embodiment, the head portion 307 is made of a material having a stiffness (i.e., Modulus of Elasticity) of at least about 100 GPa. In certain other instances, the stiffness of the material of the head portion 307 can be greater, such as at least about 110 GPa, 125 GPa, 190 GPa, and particularly within a range between about 100 GPa and about 250 GPa.

In some embodiments, it is particularly desirable to form the head portion 307 from a cobalt-containing metal. For example, in one particular embodiment, the head portion 307 includes cobalt chromium molybdenum (CCM), such that the entire head portion 307 is made entirely of CCM. Use of such materials within the head portion 307, particularly CCM, provides superior mechanical properties and improved imaging properties over materials such as stainless steel. Additionally, it has been observed that use of CCM, improves the lifetime of the implant since it has lower galvanic corrosion potential when coupled with other metals.

Figure 6:
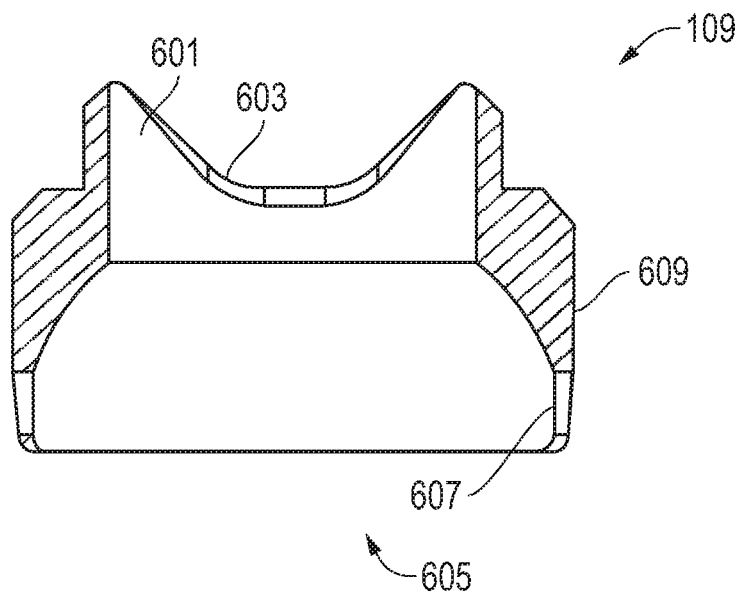
FIG. 6 includes a cross-sectional view of a crown in accordance with an embodiment.

FIG. 6 includes a cross-sectional view of a crown configured to be engaged within an interior of the head portion in accordance with an embodiment. As illustrated, the crown 309 has a unique shape such that it can be disposed between the screw head 305 and the rod and engaged with both the screw head 305 and the rod when assembled. As noted herein, the crown 309 is configured to be housed within the interior of the head portion 307 of the receiving portion 301, and includes side surfaces 609 for engaging interior surfaces of the head portion 307.

The crown 309 includes an opening 605 for engagement of the screw head therein. As such, the opening 605 can have a semi-hemispherical shape defined by surface 607 such that it can directly contact and engage the screw head. Additionally, the crown 309 includes a saddle portion 601 configured to engage a surface of the rod. Notably, the saddle portion 601 includes a saddle surface 603 configured to directly contact and engage a portion of the rod within the interior of the head portion 307.

Like the head portion 307, the crown 309 can be formed of a material that is different than the material of other components, for example, the material of the screw 303 or the head portion 307. For example, the crown 309 can include a material that is different than a material of the screw 303, and more particularly, the material of the crown 309 can be different than the material of the head portion 307. In fact, like the head portion 307, the crown 309 can be made of a material suitable for engaging a variety of rod types thereby facilitating greater flexibility in the surgeons choice of rod. As such, the crown 309 can be made of a material having a yield strength that is less than the yield strength of the screw 303, and more particularly the screw head 305. Such a crown 309 is conducive for deformation of either the crown 309 relative to the screw head 305 and rod, which facilitates increased surface contact between the rod, crown 309, and screw head 305, thus locking the components together relative to each other. Some Suitable materials for the crown 309 comprise metal and metal alloys including materials such as titanium, steel, cobalt, chromium, cobalt chromium molybdenum and alloys or combinations thereof. In certain embodiments, the crown 309 is made entirely of cobalt chromium molybdenum.

In some alternative embodiments, the crown 309 can be made of a material having a yield strength and stiffness that is between the yield strength and stiffness of the material of the head portion 307 and the screw 303, such that it facilitates a load sharing design. For example, the crown 309 can be made of a material having a yield strength and stiffness that is less than the yield strength and stiffness of the head portion 307 and at least the same as and preferably greater than the yield strength and stiffness of the screw 303. For example, the crown 309 may be made of a titanium material having at least the same yield strength and stiffness of the material of the screw 303, but a yield strength and stiffness less than the yield strength and stiffness of the material of the head portion 307. Thus in situations of excess loading of the anchor, certain components such as the screw 303 and the crown 309 are more likely to undergo deformation before the head portion 307, thus improving the overall mechanical integrity and extending the lifetime of the anchor 300 in situations of excess loading.

Figure 7:
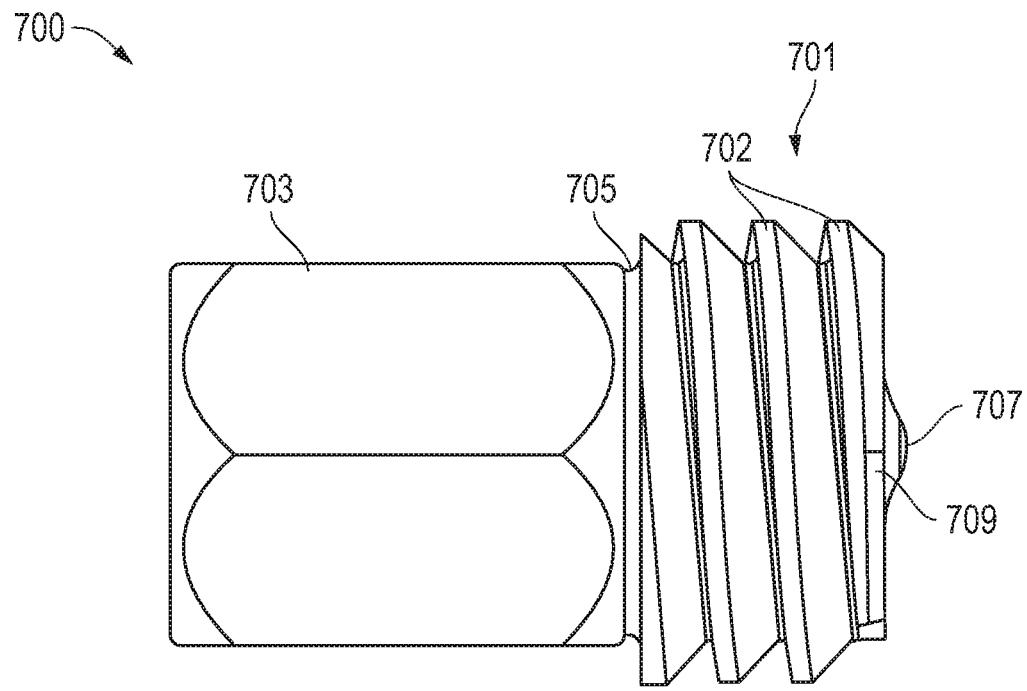
FIG. 7 includes a side view of a set screw in accordance with an embodiment.

FIG. 7 includes a side view of a set screw in accordance with an embodiment. The set screw is configured to be threaded and fastened within complementary threads of the threaded portion 515 of head portion 307 after placing the rod within the opening 313 of the head portion 307 to fixably engage and secure the rod within the receiving portion 301 of the anchor. As illustrated in FIG. 7, the set screw 700 includes a cap 703 for coupling of the set screw with a tool for insertion of the set screw 700 within the head portion 307. Notably, the set screw 700 can include a threaded portion 701 that includes threads 702 and a tip 707 at a distal end configured to engage a rod upon full and proper placement of the set screw 700 within the head portion 307. Additionally, the set screw can include a bearing surface design at the distal end such that as the set screw 700 is tightened it moves as a lower torque, turning over the surface of the rod. In accordance with one embodiment, the threaded portion 701 includes a Higby-style truncation 709 of the initial thread 702 which facilitates easier threading of the set screw 700 within the head portion 307. The Higby-style truncation 709 is manufactured such that the leading razor edge of the thread is removed.

The set screw 700 can further include a break off region 705 located between the cap 703 and threaded portion 701. As will be appreciated, the break off region 705 facilitates separation of the cap 703 from the threaded portion 701 upon engaging the set screw 700 at a specified torque within the head portion 307. As will be further appreciated in the accompanying description, the rod and anchor system can include a variety of set screw types depending on the select rod type thus providing the surgeon with greater flexibility in the implant design. Further description of this will be presented herein.

Referring briefly again to FIG. 3, the anchor 300 can include a ring 311 disposed within an anterior of the head portion 307. The ring can be a split ring having a gap in the circumference. In accordance with an embodiment, the ring 311 can be selected such that it is made of a material that is different than a material of the screw 303. Notably, the ring can be made of a metal or metal alloy comprising materials such as titanium, cobalt, chromium, steel, cobalt chromium molybdenum, and alloys or combinations thereof. In particular instances, the ring 311 can include a material having a yield strength that is the same as or greater than the yield strength of the material of the screw.

Figure 8:
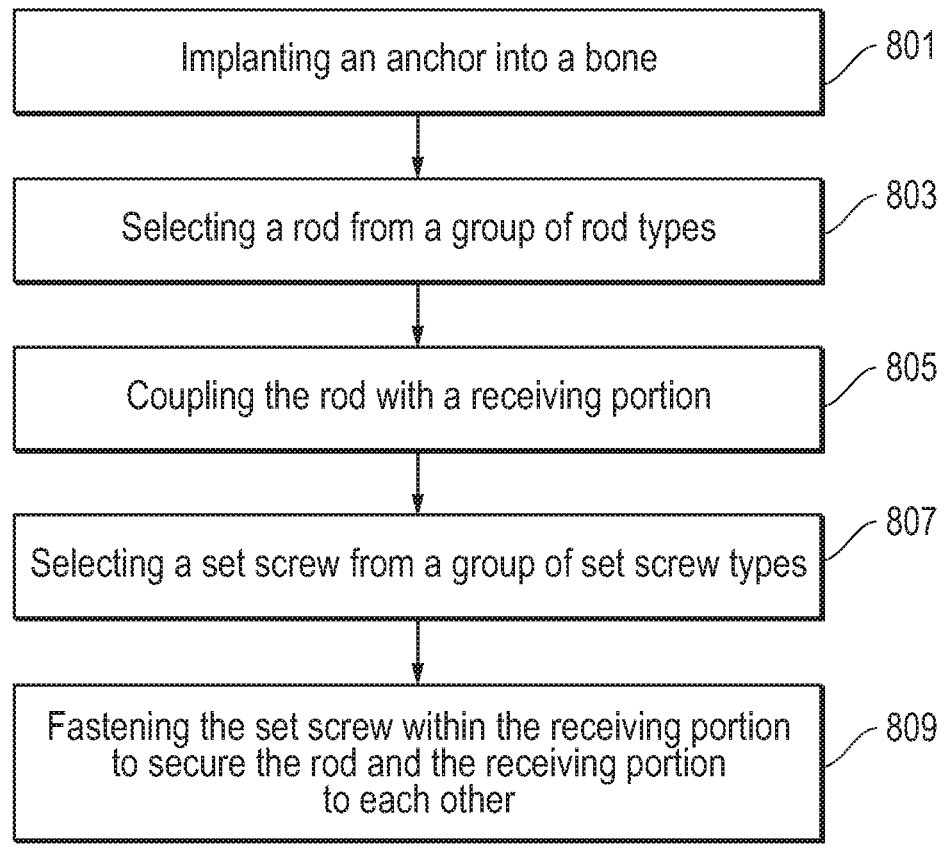
FIG. 8 includes a method of conducting a surgery using a rod and anchor system in accordance with an embodiment.

The following is directed to methods for using the anchors to conduct a surgery and correction of spinal abnormalities. FIG. 8 includes a method for conducting a surgery using anchors and rods in accordance with an embodiment. The process is initiated at step 801 by implanting an anchor 300 into a bone, which can include threading the threaded portion 306 of the screw 303 into the bone. As will be appreciated, the anchors are particularly designed to be implanted into the bone of the spine, for example, the pedicle.

Moreover, the implanting process can include an imaging process, in which the placement of the screw is aided by x-ray imaging for proper placement of the anchor in the bone. Imaging processes are particularly useful in spinal surgeries where small dimensions separate bone and critical anatomical features, such as the spinal cord. In particular, use of the anchors having the materials described herein, notably the combination of CCM and titanium, facilitates placement of the screws via imaging, since such materials are readily identifiable with imaging technologies.

After implanting the anchor into the bone at step 801, the process continues at step 803 by selecting a rod from a group of rod types. Notably, such a selection process can be based upon a diagnosis by a doctor of the condition of the spine, an evaluation of criteria such as the age and size of the patient, and the desired amount of correction, which can dictate use of one rod type over another rod type. In particular, rod types can refer to rods having different diameters as well as rods made of different materials. For example, in accordance with an embodiment, the rod and screw system disclosed herein includes two rod types with respect rod diameter. For example, one rod type includes small diameter rod type having diameters within the range between 4 mm and 5 mm. According to one particular embodiment, the small diameter rod type has an average diameter of 4.75 mm. Such rods may be particularly useful on children, adolescents, and adults, and conditions where the rod and anchor system requires less rigidity or an implant architecture having lesser mechanical demands. Accordingly, the ability to change the rod type interoperatively allows for greater flexibility in the treatment options for a greater range of patients, without concerns of needing to change any implanted anchors, since the anchors are suitable for use with a variety of rod types.

In accordance with another embodiment, the rod and anchor system herein includes large diameter rod types which may be suitable for large adults or deformities requiring stiffer rod architecture or even deformities requiring greater correction. As such, the large diameter rod type can have an average diameter within a range between about 5 mm and 6.5 mm. In accordance with one particular embodiment, the large diameter rod type has an average diameter of approximately 5.5 mm, approximately 6.1 mm, or approximately 6.3 mm.

In addition to selection of rod type based upon average diameter of the rods, a surgeon may also select a rod type based upon the material. Certain spinal conditions may dictate use of one material over another. For example, certain conditions may dictate a greater correction of the spinal abnormality, such as extreme spinal curvatures, and thus a stiff rod material may be more suitable. Other spinal conditions may dictate a less rigid rod and anchor design, for example in instances of slight abnormalities where the surgeon may wish to stabilize the spine while avoiding stress shielding effects.

As such, in accordance with one embodiment, the rod and anchor system herein includes a variety of rod types made from different materials including for example, metals, metal alloys, ceramic materials, plastic materials (e.g., including reinforced materials), and a combination thereof. In particular, such suitable metal materials can include titanium, cobalt, chromium, iron (e.g., steel), cobalt chromium molybdenum, and alloys and combinations thereof. Suitable polymer materials can include polyether materials including polyetherketone (PEK), polyetheretherketone (PEEK), polyetherketoneketone (PEKK), polyaryletherketone (PAEK). According to one particular embodiment, the rod material includes PEEK, and more particularly may include a form of reinforced PEEK, using carbon-containing reinforcing members or other ceramic materials (e.g., oxides, carbides, borides, and nitrides) as reinforcing members.

Moreover, certain rod types can include rod subtypes based upon the processing conditions of the material, such that for a given rod type, different mechanical properties of the rod can exist based upon the processing conditions used to form the rod. For example, a metal rod type (e.g., titanium alloy) may include multiple subtypes based upon the processing conditions of the material of the rod that can impart different mechanical characteristics. Certain rod subtypes can include rods formed from a multiple annealing process, single annealing process, or hot working or warm working process. Hot working and warm working processes are rudimentary shaping processes used to give a material an initial strength. Further processes such as annealing processes can remove residual stresses within the material and change the mechanical characteristics such as yield strength. For example, metal rods of the multiple annealing subtype can have a lower yield strength as compared to rods formed from a single annealing process, while rods formed with higher carbon and nitrogen contents have greater yield strength as compared to rods formed according to a lower carbon and nitrogen content material. Accordingly, within each of the rod types that differ based upon material, there may be a plurality of subtypes, wherein each subtype has different mechanical characteristics (e.g., yield strength) based upon different manufacturing processes. As will be appreciated, this provides a surgeon with greater flexibility in the selection of the rod material and thus greater flexibility in the implant design.

In particular instances, certain components of the screw 300 can include the same material, that is for example, the head portion 307 and the threaded portion 306 can include a same material, for example each can be made of pure titanium. However, the head portion 307 can be manufactured in a different manner such that it is of different subtype, and can have a greater yield strength than the pure titanium material of the threaded portion 306. It will be appreciated that such differences in subtypes of materials based on differences in manufacturing can be applied to other components of the screw 300.

After selecting a rod from a group of rod types, at step 803, the process can continue at step 805 by coupling the select rod with the receiving portion of the anchor. As will be appreciated, this can include placing a portion of the rod within the opening 313 of the head portion 307.

After coupling the rod with the receiving portion at step 807, the process can continue at step 806 by selecting a set screw from a group of set screw types based upon a material of the rod. Like the rod types, the set screw types can use different materials. Accordingly, selection of an appropriate set screw type can be based upon the material of the rod, such that the set screw can be matched to the rod. Matching of the set screw type with the rod type does not necessarily mean exact matching of both of the materials. Rather, matching includes selection of a set screw suitable for coupling the rod with the anchor without significant deformation or fatigue to the rod material or the receiving portion components of the anchor. In accordance with an embodiment, matching includes selecting a set screw based upon the yield strength and/or stiffness of the material of the set screw and the yield strength and/or stiffness of the material of the rod. For example, a set screw can be selected such that it is made of a material having a yield strength within about 800 MPa of the yield strength of the rod material. In other instances, this difference in yield strength and may be less, such that difference between the yield strength and of the set screw material and rod material is not greater than about 600 MPa, about 400 MPa, or even not greater than about 200 MPa. Certain embodiments utilize matching of materials such that the difference in yield strength is within a range between about 50 MPa and about 800 MPa, and more particularly within a range between about 50 MPa and about 400 MPa.

For example, in one particular embodiment, the rod can be made of CCM, while the set screw is selected such that it matched to the rod material and as such can include a material such as titanium. In such embodiments, depending upon the processing of the materials of the components (i.e., the subtype) the yield strengths of the materials of the set screw and the rod are within 800 MPa of each other. Notably, the set screw material is typically selected such that it is made of a material having a lesser yield strength than that of the rod such that upon excess loading, the set screw can deform around the rod, thus increasing the surface area contact between the set screw and the rod, while also avoiding permanent deformation of the rod material.

In instances where a difference does exist between the yield strength and/or stiffness of the material of the set screw and the rod, it may be particularly suitable that the yield strength and/or stiffness of the set screw is greater than that of the rod. For example, if a surgeon selected a titanium alloy rod, for example Ti6Al4V, the surgeon may select a set screw made of the same titanium alloy. Such a selection may be particularly suitable in shorter cases where little or no deformation between the components can be tolerated. Still, however, in certain other instances, such as instances of longer and greater deformity wherein the rod extends along a greater length of the spine, a set screw made of cobalt chromium molybdenum (CCM) may be selected. Such a set screw has a greater yield strength and/or stiffness than the titanium alloy rod and may ensure proper rigid engagement between the anchor and rod. As such, based on the surgeons selection of rod type and rod subtype, a set screw of different material maybe used to provide the best connection between the anchor, rod, and set screw.

After selecting a set screw from a group of set screw types at step 807, the process continues by fastening the set screw within the receiving portion to secure the rod and the receiving portion to each other. As will be appreciated, such a process in the context of break off set screws can include fastening the set screw into place until it engages a portion of the rod and the cap of the set screw is broken off.

Figure 9:
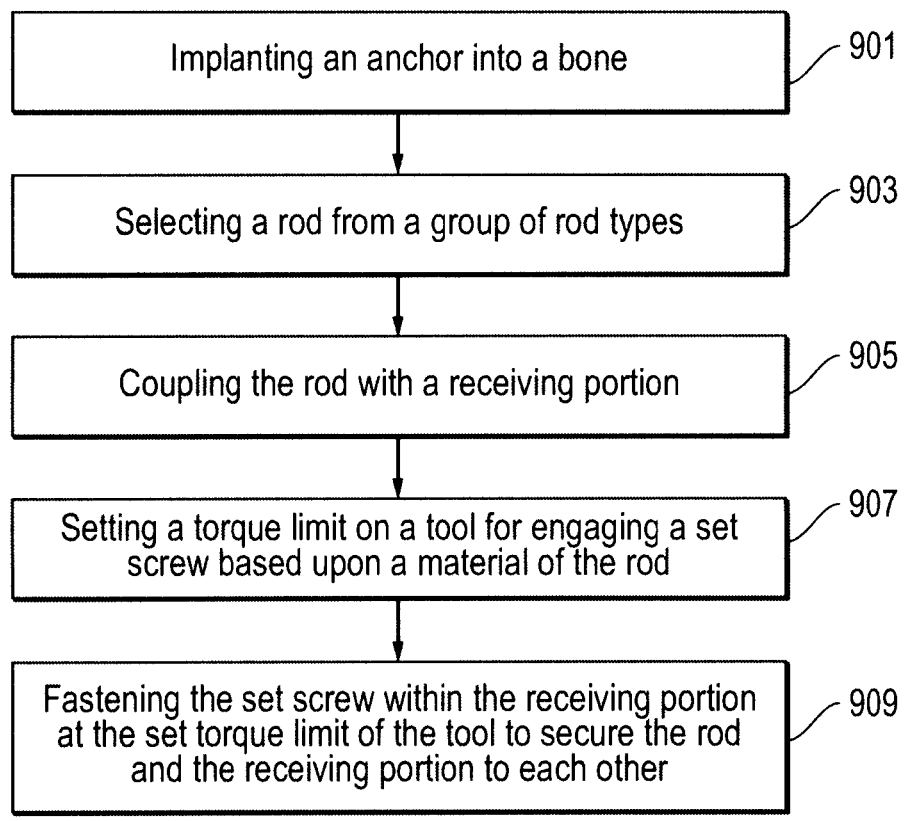
FIG. 9 includes a method of conducting a surgery using a rod and anchor system in accordance with an embodiment.

FIG. 9 includes an alternative method of correcting a spinal abnormality using a rod and anchor system. The steps 901, 903, and 905 are the same as those previously presented in FIG. 8 in corresponding steps 801, 803 and 805. At step 907, however, the method differs since the surgeon does not select a set screw from a group of set screw types. Rather, a torque limit of a tool designed to engage the set screw is set at a particular torque limit based upon a material of the rod selected. Notably, in this embodiment, the rod and anchor system may not necessarily provide the surgeon with a selection of different set screw types, and instead, this particular rod and anchor system can include a single type of set screw. In such embodiments, it may be suitable that the set of set screws are made of a material that is different than that of the screw 303. In more particular instances, it may be suitable that the set screw is made of a metal or metal alloy having a suitably high yield strength and stiffness. According to one embodiment, the rod and anchor system includes a set screw made entirely of CCM, stainless steel, or a titanium alloy.

After setting the torque limit on the tool, the process continues at step 909 by fastening the set screw within the receiving portion of the anchor to secure the rod and receiving portion to each other. Notably, the set screw is tightened at the set torque limit of the tool that was previously selected based upon the rod material. Upon reaching the set torque limit, the torque limiting handle will no longer be able to apply a torsional force to the set screw, and thus the set screw will be set at the predetermined set toque limit. Thus a single type of set screw can be used to fasten a PEEK rod, a titanium rod, or CCM rod. For example, in such instances where the surgeon wishes to fasten a PEEK rod, the torque limit may be set particularly low to avoid over-stressing and mechanical failure of the PEEK rod by the rigid metal set screw. In other instances, such as those wherein a stainless steel rod is coupled to the anchor, the torque limit of the tool can be set to a higher torque than that used to couple the PEEK rod, since the stainless steel material has a greater rigidity and is less likely to fatigue or fail under greater loading by the set screw.

In accordance with a particular embodiment, the rod and anchor system described herein can include a chart, suitable for indicating the desired torque limit for setting of the set screw based on rod types and rod subtypes. As will be appreciated, in the instances that the rod and anchor system includes a plurality of set screw types, the process of selecting a set screw type may also use a chart. The chart can be used as a reference to aid matching of the set screw types with the various rod types and rod subtypes. A combination of the above systems can be used, such that a variety of set screw types are provided and combined with a tool capable of having torque limit settings. In such instances, a chart can be provided that includes matching of a set screw type based on a rod type and rod subtype as well as the select torque limit range of the tool for proper setting of the set screw.

The foregoing has described a rod and anchor system having a combination of features distinguished over conventional rod and anchor systems. Notably, the rod and anchor system includes an anchor having a receiving portion and screw that include different components and such components intentionally incorporate different materials such that the anchor is universally coupleable with a variety of rod types without being susceptible to deformation while also having improved imaging quality. Additionally, the anchors disclosed herein have smaller receiving portions, thereby reducing the irritation by the anchor to surrounding bone and tissue. Moreover, the anchors herein use a combination of materials having lower galvanic corrosion potential compared to stainless steel, thereby extending the lifespan of the implant.

The rod and anchor system described herein use a single anchor type coupleable with a variety of rod types and rod subtypes providing the surgeon with greater versatility interoperatively. This versatility is further improved by the use of a plurality of set screw types, or alternatively a single set screw type coupleable with the anchor and rod at a select torque limit.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:
1. A method comprising:
 implanting an anchor into a bone, wherein the anchor comprises a receiving portion and a screw, the receiving portion comprising a pair of spaced apart arms defining an inner surface defining a first cavity having a crown disposed therein and a U-shaped second cavity, the screw comprising a screw head contained within the first cavity such that a portion of the screw head engages the crown and another portion of the screw head engages the inner surface, wherein the anchor is a polyaxial screw that allows the screw to pivot with respect to the receiv- ing portion, the anchor comprising a ring positioned within a recess in the first cavity that engages the screw head to retain the screw head in the first cavity, the ring being spaced apart from the crown when the screw head and the crown are positioned in the first cavity and the ring is positioned within the recess, wherein the receiving portion comprises a material having a greater yield strength than a material of the screw;

selecting a rod from a group of rod types, containing at least a first rod and a second rod wherein the first rod has a different modulus of elasticity than the second rod;

positioning the first rod within the second cavity, and selecting a set screw to secure the first rod to the receiving portion.

2. The method of claim 1, wherein the screw head comprises a material having a greater stiffness than the material of the screw.

3. The method of claim 2, wherein the screw head material comprises a stiffness is at least about 100 GPa.

4. The method of claim 1, wherein:
the receiving portion is monolithic;
the crown is monolithic; and
the receiving portion comprises cobalt chromium molybdenum and the crown comprises titanium.

5. The method of claim 1, wherein:
the screw comprises a tip opposite the screw head, a first threaded portion between the tip and the screw head and a second threaded portion between the first threaded portion and the tip;
the first threaded portion comprises a thread form of tightly wound threads along a shaft of the screw such that no gaps exist exposing the shaft between the threads; and
the second thread form includes gaps between adjacent threads of the second thread form such that the shaft of the screw is exposed between the threads of the second thread form.

6. The method of claim 1, wherein the inner surface defines a ledge extending perpendicular to the arms, the first cavity is in communication with a distal opening having a maximum width that is greater than that of the crown and the method further comprises:
bottom loading the crown through the opening and into the first cavity such that an upper surface of the crown engages the ledge.

7. The method of claim 1, wherein the set screw comprises a material having a modulus of elasticity that is equal to a modulus of elasticity of the material of the screw.

8. The method of claim 1, wherein the set screw comprises a material having a modulus of elasticity that is different from the modulus of elasticity of the first rod.

9. The method of claim 1, further comprising bottom loading the ring through a distal opening in the receiving portion and positioning the ring in the recess in the first cavity such that the ring engages the screw head to retain the screw head within the first cavity.

10. A method comprising:
implanting an anchor into a bone, wherein the anchor comprises a receiving portion and a screw, the receiving portion comprising a pair of spaced apart arms defining an inner surface defining a first cavity having a crown disposed therein and a U-shaped second cavity, the screw comprising a screw head contained within the first cavity such that a portion of the screw head engages the crown and another portion of the screw head engages the inner surface, wherein the anchor is a polyaxial screw that allows the screw to pivot with respect to the receiving portion, the anchor comprising a ring positioned within a recess in the first cavity that engages the screw head to retain the screw head in the first cavity, the ring being spaced apart from the crown when the screw head and the crown are positioned in the first cavity and the ring is positioned within the recess, wherein the receiving portion and the screw comprise a different material;

selecting a rod from a group of rod types, containing at least a first rod and a second rod wherein the first rod has a different modulus of elasticity than the second rod;

positioning the first rod within the second cavity, and selecting a set screw to secure the first rod to the receiving portion.

11. The method of claim 10, wherein the receiving portion comprises a material having a yield strength greater than a yield strength of a material of the rod.

12. The method of claim 10, wherein the receiving portion comprises a material having a yield strength greater than a yield strength of the material of the screw.

13. The method of claim 10, wherein:
the screw head comprises a stepped portion defined by a series of spaced apart concentric ridges;
the crown engages the ridges on the screw head; and
compressing the crown with the screw head locks the position of the anchor relative to the rod.

14. The method of claim 13, wherein the crown comprises a material different than a material of the receiving portion.

15. The method of claim 10, further comprising:
selecting a set screw from a group of set screw types consisting of set screws made of different materials; and
fastening the set screw within the receiving portion to secure the rod and the receiving portion to each other.

16. The method of claim 15, wherein the set screws are break off set screws and each comprise:
a threaded portion comprising a truncated initial thread such that a leading razor edge of the initial thread is removed; and
a central tapered tip extending outwardly from a distal end surface.

17. The method of claim 10, further comprising:
placing a set screw within the receiving portion;
setting a torque limit on a tool for engaging the set screw based upon a material of the rod; and
fastening the set screw within the receiving portion to secure the rod and the receiving portion to each other, wherein the set screw is tightened at the set torque limit of the tool.

18. The method of claim 10, wherein the set screw is comprised of a material having a modulus of elasticity that is different from the modulus of elasticity of the first rod.

19. A method comprising:
implanting an anchor into a bone, wherein the anchor comprises a receiving portion comprising a pair of spaced apart arms defining an inner surface defining a first cavity having a crown disposed therein and a U-shaped second cavity, the first cavity defining a longitudinal axis and containing a screw therein such that a portion of the screw engages the crown and another portion of the screw engages the inner surface, wherein the anchor is a polyaxial screw that allows the screw to pivot with respect to the receiving portion 360° about the longitudinal axis, the anchor comprising a ring positioned within a recess in the first cavity that engages a head of the screw to retain the head in the first cavity, the ring being spaced apart from the crown when the screw head and the crown are positioned in the first cavity and the ring is positioned within the recess;

selecting a rod from a group of rod types containing at least a first rod and a second rod wherein the first rod has a different modulus of elasticity than the second rod;

positioning the first rod within the second cavity such that the first rod engages a concavely curved saddle surface of the crown;

selecting a set screw from a group of set screw types; and fastening the set screw within the receiving portion to secure the rod and receiving portion to each other.

20. The method of claim 19, wherein the set screw is selected based on a material of the rod, wherein each set screw type is made of a different material and the set screw comprises a modulus of elasticity that is different from the modulus of elasticity of the first rod.

* * * * *